US010869876B2

(12) United States Patent
Itsuji et al.

(10) Patent No.: US 10,869,876 B2
(45) Date of Patent: *Dec. 22, 2020

(54) ROCURONIUM PREPARATION WITH IMPROVED STABILITY

(71) Applicant: MARUISHI PHARMACEUTICAL CO., LTD., Osaka (JP)

(72) Inventors: Yutaka Itsuji, Osaka (JP); Hironori Nagahara, Osaka (JP); Keisuke Jinbo, Osaka (JP)

(73) Assignee: MARUISHI PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/319,919

(22) PCT Filed: Jun. 26, 2014

(86) PCT No.: PCT/JP2014/067023
§ 371 (c)(1),
(2) Date: Dec. 19, 2016

(87) PCT Pub. No.: WO2015/198456
PCT Pub. Date: Dec. 30, 2015

(65) Prior Publication Data
US 2017/0128463 A1    May 11, 2017

(51) Int. Cl.
| A61K 31/58 | (2006.01) |
| A61K 9/08 | (2006.01) |
| A61K 47/12 | (2006.01) |
| A61K 31/5355 | (2006.01) |
| A61K 47/18 | (2017.01) |
| A61K 9/00 | (2006.01) |
| A61K 47/02 | (2006.01) |

(52) U.S. Cl.
CPC ............ *A61K 31/58* (2013.01); *A61K 9/0019* (2013.01); *A61K 9/08* (2013.01); *A61K 31/5355* (2013.01); *A61K 47/02* (2013.01); *A61K 47/12* (2013.01); *A61K 47/18* (2013.01)

(58) Field of Classification Search
None
See application file for complete search history.

(56) References Cited

U.S. PATENT DOCUMENTS

| 2006/0058275 A1 | 3/2006 | Friedman et al. | |
| 2007/0258908 A1 | 11/2007 | Lanza et al. | |
| 2013/0005681 A1* | 1/2013 | Su ............... | A61K 9/19 514/54 |
| 2015/0216979 A1* | 8/2015 | Bejar ............ | A61P 21/02 514/171 |
| 2016/0143919 A1* | 5/2016 | Jinbo ............ | A61K 9/0019 514/176 |

FOREIGN PATENT DOCUMENTS

| CN | 1864667 | 11/2006 |
| CN | 101843593 | 9/2010 |
| CN | 103462885 | 12/2013 |
| EA | 009079 | 4/2006 |
| EP | 2 712 611 | 4/2014 |
| EP | 3 017 817 | 5/2016 |
| NZ | 714485 | 11/2015 |
| RU | 2260013 | 12/2003 |
| RU | 2 510 263 | 5/2012 |
| WO | 01/40316 | 6/2001 |
| WO | 2004/075918 | 9/2004 |
| WO | 2008/065142 | 6/2008 |
| WO | 2009/129437 | 10/2009 |

OTHER PUBLICATIONS

Ruzin, Buffers (1999), accessed from the Internet from http://microscopy.berkeley.edu/Resources/-instruction/buffers.html, on Jul. 9, 2012.*
International Search Report dated Aug. 12, 2014 in International Application No. PCT/JP2014/067023.
Pharmaceutical Interview Form ESLAX 25 mg/2.5 mL, 50 mg/5.0 mL, Revised in Jun. 2014 (rev. ver. 7), with partial English translation.
International Preliminary Report on Patentability dated Dec. 29, 2016 in International Application No. PCT/JP2014/067023.
First Examination Report dated Dec. 14, 2017 in New Zealand Application No. 725625.
Natalia Valadares de Moraes et al., "Analysis of rocuronium in human plasma by liquid chromatography-tandem mass spectrometry with application in clinical pharmacokinetics", Journal of Pharmaceutical and Biomedical Analysis, 2014, vol. 90, pp. 180-185.
C. Farenc et al., "Quantitative determination of rocuronium in human plasma by liquid chromatography-electrospray ionization mass spectrometry", Journal of Chromatography A, 2001, vol. 910, pp. 61-67.
A.B. Chiarella et al., "Comparison of four strategies to reduce the pain associated with intravenous administration of rocuronium", British Journal of Anaesthesia, 2003, vol. 90, No. 3, pp. 377-379.
Extended European Search Report dated Oct. 17, 2017 in European Patent Application No. 14896096.6.
Office Action dated May 15, 2018 in corresponding Russian Patent Application No. 2017102325, with English Translation.

(Continued)

*Primary Examiner* — David J Blanchard
*Assistant Examiner* — Daniel F. Coughlin
(74) *Attorney, Agent, or Firm* — Wenderoth, Lind & Ponack, L.L.P.

(57) ABSTRACT

The present invention provides a rocuronium preparation with an excellent stability. The rocuronium preparation contains rocuronium and a buffer solution and having an adjusted pH of 3.5 or less (for example, 2.5 to 3.5). The buffer solution may be a citric acid-sodium hydroxide buffer solution, a tartaric acid-sodium hydroxide buffer solution, a potassium hydrogen phthalate-hydrochloric acid buffer solution, a glycine-hydrochloric acid buffer solution, or the like. Such a rocuronium preparation has, for example, after 6-month storage at 40° C., a generation rate of rocuronium-related substance C of 5% or less.

10 Claims, 1 Drawing Sheet

(56) References Cited

OTHER PUBLICATIONS

Search Report dated Jan. 16, 2020 in corresponding Russian Patent Application No. 2019134047, with English Translation.
Decision to Grant dated Aug. 28, 2019 in corresponding Russian Patent Application No. 2017102325, with English Translation.

* cited by examiner

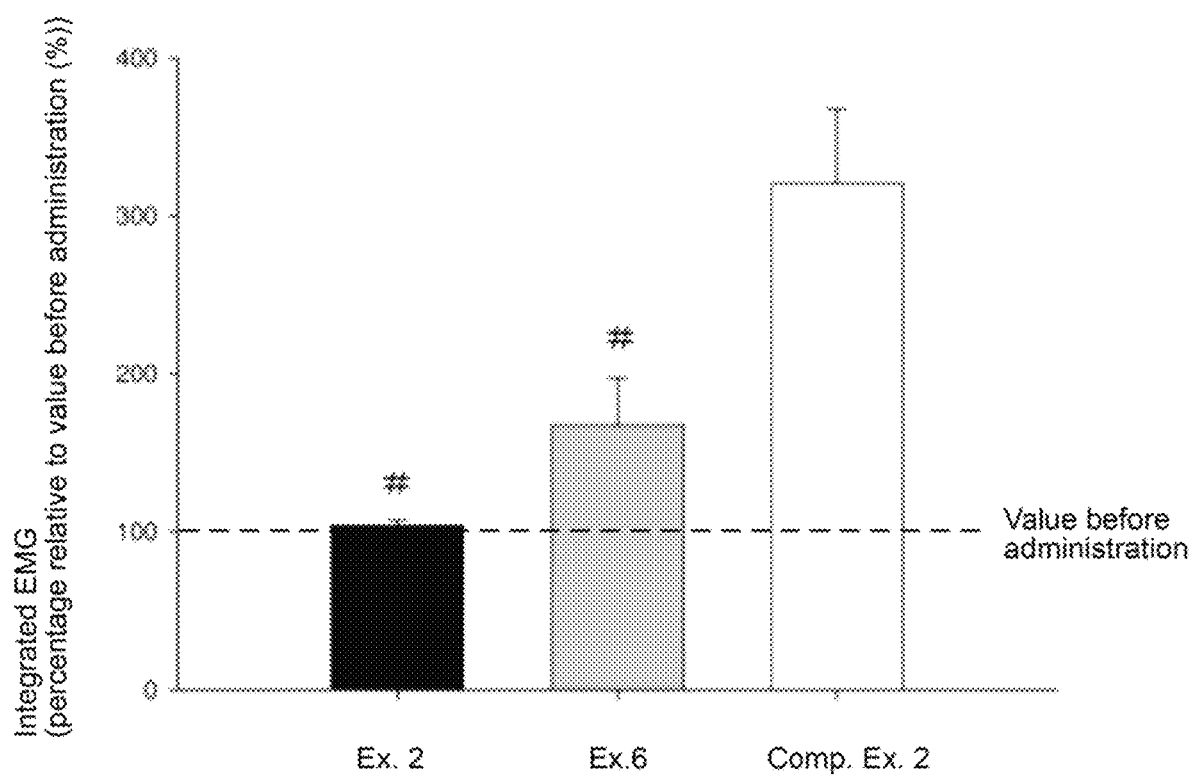

ROCURONIUM PREPARATION WITH IMPROVED STABILITY

TECHNICAL FIELD

The present invention relates to a rocuronium preparation with an improved stability, and a method for improving the stability of a rocuronium preparation.

BACKGROUND ART

Rocuronium (or rocuronium bromide) is known as an active ingredient of an anesthetic muscle relaxant or the like (Non Patent Literature 1).

Rocuronium is relatively, thermally unstable in an aqueous solution, and therefore, the storage and/or transportation thereof is troublesome and costly. For example, ESLAX, which is known as a commercially available rocuronium preparation, needs to be refrigerated at 2 to 8° C. (Non Patent Literature 1).

For the reason, attempts have been made to improve the stability of rocuronium in an aqueous solution. For example, WO 2008/065142 (Patent Literature 1) discloses a technique to stabilize a rocuronium-containing aqueous solution by adding, to the solution, a sulfoalkyl ether-β-cyclodextrin derivative or pharmaceutically acceptable salt thereof.

However, the technique of the document needs a sulfoalkyl ether-β-cyclodextrin derivative or pharmaceutically acceptable salt thereof, of which use has been reported to cause renal dysfunction etc. The document describes that the pH should be in the range of 3.5 to 7.5, and preferably 5.5 to 7.5 for reducing injection pain. In other words, in the document, the occurrence of injection pain in the pH range of 3.5 to 7.5 is recognized, and lowering the pH to 3.5 or less is not considered.

CITATION LIST

Patent Literature

Patent Literature 1: WO 2008/065142

Non Patent Literature

Non Patent Literature 1: Drug interview form of ESLAX Intravenous 25 mg/2.5 mL and ESLAX Intravenous 50 mg/5.0 mL, revised in October, 2010

SUMMARY OF INVENTION

Technical Problem

An object of the present invention is to provide a rocuronium preparation with an excellent stability.

Another object of the present invention is to provide a rocuronium preparation of which pH change is highly reduced.

Another object of the present invention is to provide a rocuronium preparation which does net cause irritation of blood vessels when administered.

Another object of the present invention is to provide a rocuronium preparation causing no or less injection pain.

Solution to Problem

To achieve the above objects, the present inventors conducted intensive investigations and found that a rocuronium preparation containing rocuronium and a buffer solution and having a pH within a certain range further lower than the pH of the commercially available product ESLAX (pH 4.0) surprisingly shows a markedly increased or improved stability and that despite the low pH, such a rocuronium preparation does not have physiologically harmful effects and therefore can be safely administered while the stability of the preparation is improved or increased. Based on the findings, the present inventors completed the present invention.

That is, the rocuronium preparation of the present invention contains rocuronium and a buffer solution, and has a pH within a predetermined range (for example, 3.5 or less). The pH of the rocuronium preparation may be, in particular, about 2.5 to 3.5 (for example, 2.8 to 3.2).

The buffer solution is not particularly limited as long as it can achieve the desired pH of the present invention, and may be at least one kind selected from a formate buffer solution, an acetate buffer solution, a phthalate buffer solution, a phosphate buffer solution, a citric acid-phosphate buffer solution, and a glycine buffer solution. In particular, the buffer solution may be at least one kind selected from a citric acid-sodium hydroxide buffer solution, a tartaric acid-sodium hydroxide buffer solution, a potassium hydrogen phthalate-hydrochloric acid buffer solution, and a glycine-hydrochloric acid buffer solution.

Typical rocuronium preparations include one having a pH of 2.5 to 3.5 and containing a glycine-hydrochloric acid buffer solution of which the concentration is 0.01 M or higher (for example, 0.015 M or higher).

The rocuronium preparation of the present invention is excellent in stability, for example, after a 6-month storage at 40° C., the generation rate of related substance C (a value obtained by subtracting the initial area percentage of the related substance C from the area percentage of the relative substance C at each measurement point) may be 5% or less.

The rocuronium preparation of the present invention may be an injection preparation. Such an injection preparation has, in addition to stability, an effect that injection pain and vascular irritation (the irritation of blood vessels) is prevented or reduced. Accordingly, the rocuronium preparation (rocuronium injection preparation) of the present invention may be a rocuronium preparation which has a rate of generated rocuronium-related substance C of 5% or less after 6-month storage at 40° C. and which causes (or has a potential to cause) no or less injection pain and/or vascular irritation (in particular, both injection pain and vascular irritation).

Thus, the rocuronium preparation of the present invention has an excellent thermal stability, and therefore, may be a preparation storable, in particular, at room temperature.

In the present invention, the stability of a rocuronium preparation can be increased or improved by adjusting the pH of the rocuronium preparation to a predetermined range. In this context, the present invention also includes a method for increasing or improving the stability of a rocuronium preparation by adjusting the pH of a rocuronium preparation containing rocuronium and a buffer solution to 3.5 or less (in particular, a method for increasing or improving the stability of a rocuronium preparation so that the rate of generated rocuronium-related substance C after 6-month storage at 40° C. is 5% or less).

Also, as described above, an injection preparation of the present invention has an effect that injection pain and vascular irritation are prevented. In this context, the present invention also includes a method for preventing or reducing both injection pain and vascular irritation caused by a rocuronium injection preparation and for increasing or improving the stability of the rocuronium injection preparation so that the rate of generated rocuronium-related substance C after 6-month storage at 40° C. is 5% or less, by adjusting the pH of a rocuronium injection preparation containing rocuronium and a buffer solution to 3.5 or less.

In these methods, the preparation (rocuronium preparation or rocuronium injection preparation may be prepared so as to be storable at room temperature.

Advantageous Effects of Invention

In the present indention, a rocuronium preparation with an excellent stability (in particular, thermal stability) can be obtained by adjusting the pH to a certain range. For example, the rocuronium preparation of the present invention is hardly decomposed even when stored in non-refrigerated conditions for a long period or treated under high-temperature and high-pressure conditions. In addition, the pH change can be tightly controlled, and therefore, the rocuronium preparation is extremely stable. Accordingly, the rocuronium preparation can be stored at normal temperature, and therefore, is extremely practical.

The rocuronium preparation of the present invention does not have physiologically harmful effects (or has only minute harmful effects), and is highly practical also in this regard. For example, the rocuronium preparation of the present invention does not cause a thrombus, perivascular inflammation, or the like, and can be administered without vascular irritation. Furthermore, when administered, the preparation causes no or much less injection pain than that caused by the commercial product (ESLAX). Therefore, the rocuronium preparation of the present invention is also effective as a preparation capable of preventing or reducing injection pain and/or vascular irritation. Also, the rocuronium preparation of the present invention achieves an increased or improved stability without the component described in Patent Literature 1 (a sulfoalkyl ether-β-cyclodextrin derivative or pharmaceutically acceptable salt thereof).

Thus, the preparation of the present invention is excellent in both of stability and safety, and is an extremely useful preparation.

As described above, the preparation of the present invention does not have physiologically harmful effects, which is very surprising given the fact that the pH of the commercial rocuronium preparation (ESLAX) was decided to be a higher pH level (4.0) than the pH range of the present invention in consideration of physiologically harmful effects (cited from the review report for ESLAX).

BRIEF DESCRIPTION OF DRAWING

FIG. 1 is a graph showing EMG-based injection pain evaluation results of the preparations of Example 2, Example 6, and Comparative Example 2.

DESCRIPTION OF EMBODIMENTS

The rocuronium preparation of the present invention contains rocuronium and a buffer solution and has a pH within a predetermined range. The rocuronium is rocuronium bromide (chemical name: (+)-(17β-acetoxy-3α-hydroxy-2β-morpholino-5α-androstan-16β-yl)-1-allyl-1-pyrrolidinium bromide) represented by the following formula.

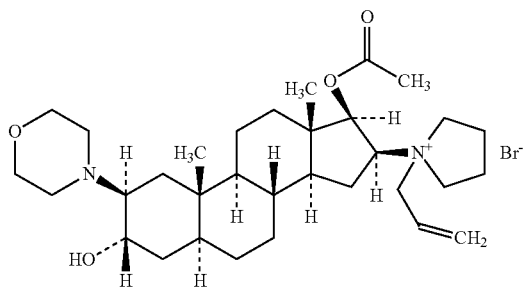

The percentage of the rocuronium in the preparation is not particularly limited and appropriately selected depending on the disease condition, the dosage form, etc. The percentage may be, for example, about 0.1 to 10% w/v, preferably about 0.5 to 5% w/v, and more preferably about 0.8 to 3% w/v.

The buffer solution is not particularly limited as long as it can achieve the desired pH of the present invention, and examples thereof include carboxylic acid buffer solutions (for example, a formate buffer solution, an acetate buffer solution, a citrate buffer solution, a tartrate buffer solution, a phthalate buffer solution, etc.), phosphate buffer solutions (for example, a phosphate buffer solution, a citric acid-phosphate buffer solution, etc.), amino acid buffer solutions (for example, a glycine buffer solution etc.), etc. In order to achieve the desired pH of the present invention, suitable buffer solutions among them may be citrate buffer solutions (for example, a citric acid-sodium hydroxide buffer solution etc.), tartrate buffer solutions (for example, a tartaric acid-sodium hydroxide buffer solution etc.), phthalate buffer solutions (for example, a potassium hydrogen phthalate-hydrochloric acid buffer solution etc.), and glycine buffer solutions (for example, a glycine-hydrochloric acid buffer solution etc.). In particular, a glycine-hydrochloric acid buffer solution may be used. These buffer solutions may be used alone or in combination of two or more thereof. These buffer solutions may be prepared ones or commercially available products.

The concentration of the buffer solution in the preparation is not particularly limited and may be appropriately selected depending on the type of the buffer solution, the desired pH, etc. The concentration may be selected from the range of 0.001 M or higher (for example, 0.003 to 0.8 M), for example, 0.005 M or higher (for example, 0.008 to 0.7 M), preferably 0.01 M or higher (for example, 0.015 to 0.5 M), more preferably 0.02 M or higher (for example, 0.03 to 0.4 M), and particularly preferably 0.04 M or higher (for example, 0.05 to 0.3 M).

In particular, when the buffer solution is a glycine-hydrochloric acid buffer solution, the concentration in the preparation may be, for example, 0.01 M or higher (for example, 0.015 to 0.8 M), preferably 0.02 M or higher (for example, 0.025 to 0.6 M), more preferably 0.03 M or higher (for example, 0.04 to 0.5 M), and in particular, approximately 0.05 M or higher (for example, 0.06 to 0.3 M).

A higher concentration of the buffer solution leads to more effective control of the change or variation of the pH of the preparation.

The concentration of a buffer solution means the concentration of the component exhibiting a buffering ability (buffering action), for example, the concentration of glycine in the case of a glycine-hydrochloric acid buffer solution.

The pH of the rocuronium preparation of the present invention may be 3.5 or less (for example, 1.8 to 3.5), preferably 3.4 or less (for example, 2 to 3.35), and more preferably 3.3 or less (for example, 2.2 to 3.3). In particular, the pH of the rocuronium preparation may be, for example, 2 to 3.5, preferably 2.5 to 3.5 (for example, 2.8 to 3.2), and usually less than 3.5 (for example, 2 to 3.4). The pH may be a value at a temperature of 20 to 30° C.

The rocuronium preparation of the present invention may contain other components (a pharmaceutical carrier etc.) blended thereinto as needed. Examples of such other components include a solvent, a solubilizing agent, a suspending agent, an isotonizing agent, a soothing agent, etc. In addition, any known additives and pharmaceutically acceptable additives usually used in the pharmaceutical field, for example, a preservative, an antioxidant, a stabilizing agent, and an oxidant inhibitor, may be used as needed. These additives may be used alone or as a mixture of two or more thereof as appropriate for the intended dosage form etc. These additives may be commercially available products.

The solvent is not particularly limited, and examples thereof include purified water, ethanol, propylene glycol, polyethylene glycol, macrogol, sesame oil, corn oil, olive oil, etc. The solubilizing agent is not particularly limited, and examples thereof include propylene glycol, D-mannitol, benzyl benzoate, ethanol, triethanolamine, sodium carbonate, sodium citrate, etc. The suspending agent is not particularly limited, and examples thereof include benzalkonium chloride, carmellose, hydroxypropylcellulose, propylene glycol, polyvinyl pyrrolidone, methyl, cellulose, glycerol monostearate, sodium lauryl sulfate, lecithin, polyvinyl alcohol, etc. The isotonizing agent is not particularly limited, and examples thereof include glucose, D-sorbisol, sodium chloride, D-mannitol, glycerol, etc. The soothing agent is not particularly limited, and examples thereof include benzyl alcohol etc.

The preservative is not particularly limited, and examples thereof include ethyl p-hydroxybenzoate, chlorobutanol, benzyl alcohol, sodium dehydroacetate, sorbic acid, etc. The antioxidant is not particularly limited, and examples thereof include sodium sulfite, ascorbic acid, etc. The stabilizing agent is not particularly limited, and examples thereof include casein, sodium caseinate, etc. Examples of the oxidant inhibitor include t-butylhydroquinone, butylhydroxyanisole, butylhydroxytoluene, α-tocopherol, and derivatives thereof.

The preparation of the present invention may contain the particular component described in Patent Literature 1, namely a sulfoalkyl ether-β-cyclodextrin derivative or pharmaceutically acceptable salt thereof, but usually need not contain the substance. Since there is no need of such a component in the present invention, a stabilized rocuronium preparation which is highly safe and free from the risks of renal dysfunction etc. can be provided.

The osmotic pressure of the rocuronium preparation of the present invention is not particularly limited, and may be, for example, 250 to 1000 mosmol/kg or 260 to 600 mosmol/kg.

The rocuronium preparation of the present invention can be produced by, for example, blending rocuronium with a buffer solution (and other components if needed), but the production method is not particularly limited thereto.

The dosage form of the rocuronium preparation of the present invention is not particularly limited, but usually a solution. Examples of the solution include parenteral preparations, such as injection preparations (for intravenous injection, intraarterial injection, intramuscular injection, subcutaneous injection, intradermal injection, intraperitoneal injection, intraspinal injection, or epidural injection), ophthalmic preparations, and intranasal preparations.

The administration route of the rocuronium preparation of the present invention is not particularly limited, but in the cases of parenteral administration using injection preparations, it is preferable to appropriately select the route from preferred routes including intravenous, intraarterial, subcutaneous, intradermal, intramuscular, and intraperitoneal administration routes depending on the age of the patient, the disease condition, and/or other conditions.

The dosage amount (dose usage) of the rocuronium preparation of the present invention varies with the age, the sex, and the weight of the patient, the severity of the disease, etc., and therefore is not particularly limited, but generally, the daily total dose of the active ingredient (namely, rocuronium) is usually about 0.01 to 100 mg, and preferably about 10 to 60 mg per adult. Also, the dosage and administration method vary with the age, the sex, and the weight of the patient, the severity of the disease, etc., and therefore is not particularly limited, but generally, it is appropriate that the daily total dose is administered once a day or administered as multiple (for example, 2 to 4) divided doses. In an exemplary method, rocuronium is intravenously administered in a dose of 0.6 mg/kg, and as needed, additionally administered by continuous infusion in a dose of 0.1 to 0.2 mg/kg during the operation.

The rocuronium preparation of the present invention is preferably used under anesthesia although it is not a necessary condition. The anesthetic is not particularly limited, and preferred examples thereof include an inhalation anesthetic and an intravenous anesthetic. The inhalation anesthetic is not particularly limited, and examples thereof include volatile inhalation anesthetics, such as halothane, isoflurane, enflurane, methoxyflurane, sevoflurane, and desflurane; and gaseous inhalation anesthetics, such as ethylene, cyclopropane, diethylether, chloroform, nitrous oxide, and xenon. The intravenous anesthetic is not particularly limited, and examples thereof include propofol, midazolam, ketamine, tiletamine, thiopental, methohexital, and etomidate. Preferred are propofol, midazolam, etc. These anesthetics may be used alone or as a mixture of two or more kinds thereof. These anesthetics may be commercially available products.

As described above, the rocuronium preparation of the present invention has a high stability. For example, after the rocuronium preparation is stored at 40° C. for 3 months, the rate of generated rocuronium-related substance C is extremely low and is 2.5% or less (for example, 0 to 2.3%), preferably 2% or less (for example, 0.1 to 1.8%), more preferably approximately 1.5% or less (for example, 0.2 to 1.3%). It is also possible to reduce the generation rate of rocuronium-related substance C to 1% or less (for example, 0.1 to 0.3%).

Also, after the rocuronium preparation is stored at 40° C. for 6 months, the rate of generated rocuronium-related substance C can be 5% or less )for example, 0 to 4.9%), preferably 4% or less (for example, 0.01 to 3.9%), more preferably approximately 3% or less (for example, 0.1 to 2.9%).

When the generation rate of rocuronium-related substance C is 5% or less, the rocuronium preparation is judged to be a pharmaceutical product storable at room temperature. Here, room temperature means 1 to 30° C. (Japanese pharmacopoeia).

Thus, the rocuronium preparation of the present invention has an extremely excellent stability, and the rate of generated rocuronium-related substance C after 3-month storage can be reduced to a far lower level than 5%, which is the boundary value between storable and not storable at room-temperature. Even after a long-term (6-month) storage, the generation rate can still be lower than 5%, showing that the preparation is storable at room temperature.

The related substance C is the main decomposition product of rocuronium, and is a substance described in the United States Pharmacopeia (USP) and the European Pharmacopoeia (EP).

After the rocuronium preparation is thermally treated at 121° C. for 20 minutes, the rate of generated rocuronium-related substance C is extremely low and is 0.7% or less (for example, 0 to 0.6%), preferably 0.5% or less (for example, 0.01 to 0.45%), more preferably approximately 0.4% or less (for example, 0.05 to 0.35%). It is also possible to reduce the generation rate of rocuronium-related substance C to 0.3% or less (for example, 0.01 to 0.3%).

In the present invention, the pH change of a rocuronium preparation can also be minimized. For example, after the rocuronium preparation is stored at 40° C. for 6 months, the pH difference (or the absolute value thereof) between before and after the storage is as low as 0.25 or less (for example, 0 to 0.22), preferably 0.2 or less (for example, 0 to 0.18), more preferably approximately 0.15 or less (for example, 0 to 0.12), and can also be 0.1 or less (for example, 0 to 0.08, preferably 0 to 0.05, more preferably 0 to 0.03). Also, in the cases where the rocuronium preparation is thermally treated at 121° C. for 20 minutes, the pH difference between before and after the thermal treatment can be selected from similar ranges.

Thus, in the present invention, a rocuronium preparation with an extremely high stability can foe obtained by adjusting the pH (as well as selecting an appropriate type of buffer solution and adjusting the concentration of the buffer solution). In this context, the present invention also includes a method for increasing or improving the stability of a rocuronium preparation by adjusting the pH of a rocuronium preparation containing rocuronium and a buffer solution to the predetermined range (for example, 3.5 or less).

The rocuronium preparation of the present invention has a relatively low pH, but does not have or hardly has physiologically harmful effects. In particular, the rocuronium preparation of the present invention is capable of preventing or reducing injection pain and/or vascular irritation with high efficiency. In this context, the present invention also includes a method for preventing or reducing (alleviating) infection pain and/or vascular irritation (in particular, both injection pain and vascular irritation) caused by rocuronium (in particular, caused by administration of a rocuronium preparation), by adjusting the pH of a rocuronium preparation (rocuronium injection preparation) containing rocuronium and a buffer solution to the predetermined range (for example, 3.5 or less).

The present invention encompasses embodiments in which various structures described above are combined within the technical scope of the present invention in such a manner that the effect of the present invention is exerted.

EXAMPLES

Hereinafter, the present invention will be illustrated in more detail by Examples, but it is not limited thereto. Various modifications can be .made within the technical idea of the present invention by those with ordinary still in the art.

In the Examples, various properties were determined or evaluated as follows.

pH

Measurement was performed at 20 to 30° C. in accordance with the "pH determination" in the Japanese Pharmacopoeia.

Concentration Rate of Related Substance (Impurity) C

Measurement was performed in accordance with the USP method for HPLC.

Vascular Irritation

Before the start of administration, hairs on the administration site of each of six (three for each group) 14-week old male JW rabbits were removed with an electric hair clipper. From near the middle of the left posterior auricular vein, a 3-cm portion having fewer branches of small vessels (retention site) was selected, and both the ends of the portion were marked with an indelible marker, which were called central and peripheral hemostatic sites. On the day of administration, under sevoflurane anesthesia (induction: 5%, maintenance: 3%), a point 5 mm peripheral to the peripheral hemostatic site was marked with the indelible marker, for use as the injection needle insertion site.

At the time of administration, a clamp was attached to a part peripheral to the injection needle insertion site in order to stop the blood flow, and the injection needle was inserted from the injection needle insertion site, toward the central side, to the peripheral hemostatic site. A sample solution in an amount of 0.025 mL was injected, and it was confirmed that the local blood vessel was filled with the sample substance. Subsequently, the central hemostatic site was closed with a clamp, additional 0.025 mL of the sample solution was injected, and the peripheral hemostatic site was closed with a clamp. Next, 0.2 ml of a 2.5% w/v sugammadex solution was promptly administered from the right auricular vein. After 3 minutes of retention of the sample solution, the clamps were removed, and after the spontaneous breathing of the animal was confirmed, the anesthesia was removed. For the daily administration of the sample solution, the same retention site and the same injection needle insertion site were used as far as possible.

Number of doses: once daily for 8 consecutive days

Administration volume: 0.05 mL/site/day

The administration method, the number of doses, the administration period, and the administration volume were selected in accordance with the method of Fukawa et al. (Nihon Yakurigaku Zasshi 71: 307-315, 1975).

The vascular irritation was evaluated once daily based on the macroscopic inspection criteria shown below.

(Thrombus)

−: no thrombus (0 mm)

+: small thrombus (1 to 4 mm)

++: medium-sized thrombus (5 to 14 mm)

+++: large thrombus (15 mm or larger)

(Inflammation Around the Blood Vessel (Hyperemia, Swelling))

−: no change

+: slight inflammation (limited to the 3 cm long hemostatic site)

++: moderate inflammation (⅓ of the auricle centering around the hemostatic site)

+++: severe inflammation (½ to the whole of the auricle)

Injection Pin

Urethane was intraperitoneally injected to rats (8-week old male SD rats, 11 animals for each group) at a dose of 1.1 g/kg, hairs around the treated area were removed, and the skin was incised to expose blood vessels near the femoral artery. A PFA tube having a tip tapered beforehand was introduced about 2 cm into the caudal superficial epigastric artery in a retrograde manner until it reached the site from which the femoral artery arises. A coaxial needle electrode (26 G) was inserted into the left posterior semitendinosus muscle. After the operation, the rats were kept at about 37° C. Before the start of administration, the baseline value was measured for 30 seconds. Each test solution in an amount of 50 82 L was administered through the PFA tube at a rate of 0.8 mL/min, and electromyography (EMG) measurement was performed over 30 seconds from the start of the administration. Each test solution was repeatedly administered at intervals of 1 hour or longer. Before the administration and after the final administration, 1% propofol "Maruishi" (Japanese product name) was administered to the rats, and only such individuals as to exhibit muscle contraction were used in the test. The analysis of the obtained electromyogram was performed using PowerLab (16sp, ADInstruments). The raw signals were rectified and integrated to give quantified data ($\mu V \cdot s$). The results are shown as percentage values relative to the value before administration as 100%.

Example 1

In water for injection, 0.06 g of glycine, 0.67 g of sodium chloride, 30 g of 0.1 M HCl, and 1.0 g of rocuronium bromide were dissolved, and water for injection, was further added to adjust the volume to 100 mL.

The pH of the obtained preparation was 2.0. After the preparation was stored at 40° C. for 3 months and 6 months, the pH and the generation rate of rocuronium-related substance C were determined. The pH was 2.0 in both cases (after 3-month storage and 6-month storage), and the generation rates of rocuronium-related substance C were 1.24% (after 3-month storage) and 2.52% (after 6-month storage).

Example 2

In water for injection, 0.55 g of glycine, 0.50 g of sodium chloride, 30 g of 0.1 M HCl, and 1.0 g of rocuronium bromide were dissolved, and water for injection, was further added to adjust the volume to 100 mL.

The pH of the obtained preparation was 3.0. After the preparation was stored at 40° C. for 3 months and 6 months, the pH and the generation rate of rocuronium-related substance C were determined. The pH was 3.0 in both cases (after 3-month storage and 6-month storage), and the generation rates of rocuronium-related substance C were 0.77% (after 3-month storage) and 1.58% (after 6-month storage).

Reference Example 1

In water for injection, 4.58 g of glycine, 30 g of 0.1 M HCl, and 1.0 g of rocuronium bromide were dissolved, and water for injection was further added to adjust the volume to 100 mL.

The pH of the obtained preparation was 4.0. After the preparation was stored for 3 months and 6 months in the same manner as in Example 1, the pH and the generation rate of rocuronium-related substance C were determined. The pH was 4.0 in both cases, and the generation rates of rocuronium-related substance C were 2.81% (after 3-month storage) and 5.36% (after 6-month storage).

Comparative Example 1

A rocuronium preparation of which the composition was identical to that of a commercial rocuronium preparation (acetate buffer solution, 0.15 M in terms of acetate ions, pH 4.0) was prepared in the same manner as in Example 1. After the preparation was stored for 3 months and 6 months in the same manner as in Example 1, the pH and the generation rate of rocuronium-related substance C were determined. The pH was 4.0 in both cases, and the generation rates of rocuronium-related substance C were 2.53% (after 3-month storage) and 5.46% (after 6-month storage).

The results are summarized in Table 1.

TABLE 1

|  | At the time of preparation | | | After 3-month storage at 40° C. | | After 6-month storage at 40° C. | |
| --- | --- | --- | --- | --- | --- | --- | --- |
|  | pH | Concentration of hydrochloric acid (M) | Concentration of glycine (M) | Generation rate of rocuronium-related substance C (%) | pH | Generation rate of rocuronium-related substance C (%) | pH |
| Ex. 1 | 2.0 | 0.03 | 0.007 | 1.24 | 2.0 | 2.52 | 2.0 |
| Ex. 2 | 3.0 |  | 0.073 | 0.77 | 3.0 | 1.58 | 3.0 |
| Ref. Ex. 1 | 4.0 |  | 0.61 | 2.81 | 4.0 | 5.36 | 4.0 |
| Comp. Ex. 1 | 4.0 | — | — | 2.53 | 4.0 | 5.46 | 4.0 |

Ex.: Example
Ref. Ex.: Reference Example
Comp. Ex.: Comparative Example

The results in Table 1 clearly show that, by adjusting the pH to the predetermined range, the generation rate of rocuronium-related substance G is markedly reduced and the stability is increased as compared to the case where the pH is 4.0.

In particular, the comparison of Example 1, Example 2, and Reference Example 1 showed a surprising behavior that, with the decrease in the pH, the generation rate of rocuronium-related substance C did not simply reduce but turned to increase. Also, in the Examples, the pH did not change, which showed that the rocuronium preparations were extremely stable. Further, the comparison of Reference Example 1 and Comparative Example 1 showed that such stability did not depend on the type of the buffer solution.

Example 3

In water for injection, 1.17 g of glycine, 0.37 g of sodium chloride, 45 g of 0.1 M HCl, and 1.0 g of rocuronium bromide were dissolved, and water for injection was further added to adjust the volume to 100 mL.

The pH of the obtained preparation was 3.0. After the preparation was thermally treated at 121° C. for 20 minutes, the pH and the generation rate of rocuronium-related substance C were determined, The pH was 3.0 and the generation rate of rocuronium-related substance C was 0.28%.

Example 4

The preparation obtained in Example 2 (pH 3.0) was thermally treated in the same manner as in Example 3, and then, the pH and the generation rate of rocuronium-related substance C were determined. The pH was 3.0 and the generation rate of rocuronium-related substance C was 2.3%.

In water for injection, 0.18 g of glycine, 0.64 g of sodium chloride, 20 g of 0.1 M HCl, and 1.0 g of rocuronium bromide were dissolved, and water for injection was further added to adjust the volume to 100 mL.

The pH of the obtained preparation was 3.0. After the preparation was thermally treated in the same manner as in Example 3, the pH and the generation rate of rocuronium-related substance C were determined. The pH was 3.1 and the generation rate of rocuronium-related substance C was 0.23%.

Comparative Example 1

The preparation obtained in Comparative Example 1 (pH 4.0) was thermally treated in the same manner as in Example 3, and then, the pH and the generation rate of rocuronium-related substance C were determined. The pH was 4.0 and the generation rate of rocuronium-related substance C was 0.75%.

The results are summarized in Table 2.

TABLE 2

|  | At the time of preparation | | | After thermal treatment at 121° C. for 20 minutes | |
| --- | --- | --- | --- | --- | --- |
|  | pH | Concentration of hydrochloric acid (M) | Concentration of glycine (M) | Generation rate of rocuronium-related substance C (%) | pH |
| Ex. 3 | 3.0 | 0.045 | 0.16 | 0.28 | 3.0 |
| Ex. 4 |  | 0.03 | 0.073 | 0.23 | 3.0 |
| Ex. 5 |  | 0.02 | 0.024 | 0.23 | 3.1 |
| Comp. Ex. 1 | 4.0 | — | — | 0.75 | 4.0 |

The results in Table 2 clearly show that, in the cases where the pH is fixed, regardless of the difference in the concentration of the buffer solution, the generation rate of rocuronium-related substance C is markedly reduced. Even after the thermal treatment, the pH was not largely changed.

Reference Example 2

In water for injection, 0.90 g of sodium chloride, 15 g of 0.1 M HCl, and; 1.0 g of rocuronium bromide were dissolved, and water for injection was further added to adjust the volume to 100 ml.

The pH of the obtained preparation was 3.0. After the preparation was thermally treated in the same manner as in Example 3, the pH was determined. The pH was 3.3.

The results of Reference Example 2 and Example 5 are summarized in Table 3.

TABLE 3

|  | At the time of preparation | | | After thermal treatment at 121° C. for 20 minutes |
| --- | --- | --- | --- | --- |
|  | pH | Concentration of hydrochloric acid (M) | Concentration of glycine (M) | pH |
| Ex. 5 | 3.0 | 0.02 | 0.024 | 3.1 |
| Ref. Ex. 2 |  | 0.015 | 0 | 3.3 |

The results in Table 3 clearly show that, without the buffering action, the pH is largely changed by thermal treatment.

Example 6

In water for injection, 0.55 g of glycine, 0.50 g of sodium chloride, 51 g of 0.1 M HCl, and 1.0 g of rocuronium bromide were dissolved, and water for injection was further added to adjust the volume to 100 mL.

The pH of the obtained preparation was 2.5. After the preparation was thermally treated in the same manner as in Example 3, the pH and the generation rate of rocuronium-related substance C were determined. The pH was 2.5 and the generation rate of rocuronium-related substance C was 0.10%.

Example 7

In water for injection, 0.55 g of glycine, 0.50 g of sodium chloride, 38 g of 0.1 M HCl, and 1.0 g of rocuronium bromide were dissolved, and water for injection was further added to adjust the volume to 100 mL.

The pH of the obtained preparation was 2.8. After the preparation was thermally treated in the same manner as in Example 3, the pH and the generation rate of rocuronium-related. substance C were determined. The pH was 2.8 and the generation rate of rocuronium-rerated substance C was 0.14%.

In water for injection, 0.55 g of glycine, 0.50 g of sodium chloride, 27 g of 0.1 M HCl, and 1.0 g of rocuronium bromide were dissolved, and water for injection was further added to adjust the volume to 100 mL.

The pH of the obtained preparation was 3.2. After the preparation was thermally treated in the same manner as in Example 3, the pH and the generation rate of rocuronium-related substance C were determined. The pH was 3.2 and the generation rate of rocuronium-related substance C was 0.27%.

Example 9

In water for injection, 0.55 g of glycine, 0.50 g of sodium chloride, 21 g of 0.1 M HCl, and 1.0 g of rocuronium bromide were dissolved, and water for injection was further added to adjust the volume to 100 mL.

The pH of the obtained preparation was 3.5. After the preparation was thermally treated in the same manner as in Example 3, the pH and the generation rate of rocuronium-related substance C were determined. The pH was 3.5 and the generation rate of rocuronium-related substance C was 0.31%.

The results are summarized in Table 4. In Table 4, the results of Example 4 and Comparative Example I, which have already been shown in Table 2, are shown together for reference.

TABLE 4

|  | At the time of preparation | | | After thermal treatment at 121° C. for 20 minutes | |
| --- | --- | --- | --- | --- | --- |
|  | pH | Concentration of hydrochloric acid (M) | Concentration of glycine (M) | Generation rate of rocuronium-related substance C (%) | pH |
| Ex. 6 | 2.5 | 0.051 | 0.073 | 0.10 | 2.5 |
| Ex. 7 | 2.8 | 0.038 |  | 0.14 | 2.8 |

TABLE 4-continued

|  | At the time of preparation | | | After thermal treatment at 121° C. for 20 minutes | |
| --- | --- | --- | --- | --- | --- |
|  | pH | Concentration of hydrochloric acid (M) | Concentration of glycine (M) | Generation rate of rocuronium-related substance C (%) | pH |
| Ex. 4 | 3.0 | 0.03 | — | 0.23 | 3.0 |
| Ex. 8 | 3.2 | 0.027 | — | 0.27 | 3.2 |
| Ex. 9 | 3.5 | 0.021 | — | 0.31 | 3.5 |
| Comp. Ex. 1 | 4.0 | — | — | 0.75 | 4.0 |

The results in Table 4 clearly show that, in the cases where the pH is in the predetermined range, regardless of the difference in the pH, the generation rate of rocuronium-related substance C is markedly reduced. In addition, there observed no significant pH change, i.e., the pH change is markedly Example 10

In water for injection, 15 g of 0.1 M hydrochloric acid, 0.45 g of sodium chloride, 0.42 g of potassium, hydrogen phthalate, and 0.50 g of rocuronium bromide were dissolved, and water for injection was further added to adjust the volume to 50 mL.

The pH of the obtained preparation was 3.0. After the preparation was thermally treated in the same manner as in Example 3, the pH and the generation rate of rocuronium-related substance C were determined. The pH was 3.0 and the generation rate of rocuronium-related substance C was 0.25%.

In water for injection, 0.45 g of sodium chloride, 0.34 g of citric acid hydrate, 2.46 g of 0.1 M sodium hydroxide solution, and 0.50 g of rocuronium bromide were dissolved, and water for injection was further added to adjust the volume to 50 mL.

The pH of the obtained preparation was 3.0. After the preparation was thermally treated in the same manner as in Example 3, the pH and the generation rate of rocuronium-related substance C were determined. The pH was 3.0 and the generation rate of rocuronium-related substance C was 0.19%.

Example 12

In water for injection, 0.45 g of sodium chloride, 0.23. g of tartaric acid, 2.50 g of 0.1 M sodium hydroxide solution, and 0.50 g of rocuronium bromide were dissolved, and water for injection was further added to adjust the volume to 50 mL.

The pH of the obtained preparation was 3.0. After the preparation was thermally treated in the same manner as in Example 3, the pH and the generation rate of rocuronium-related substance C were determined. The pH was 3.0 and the generation rate of rocuronium-related substance C was 0.28%.

The results are summarized in Table 5. In Table 5, the results of Comparative Example 1, which have already been shown in Table 2, are shown together for reference.

TABLE 5

|  | At the time of preparation | | After thermal treatment at 121° C. for 20 minutes | |
| --- | --- | --- | --- | --- |
|  | pH | Buffer solution | Generation rate of rocuronium-related substance C (%) | pH |
| Ex. 10 | 3.0 | Hydrochloric acid-potassium phthalate | 0.25 | 3.0 |
| Ex. 11 | | Citric acid-sodium hydroxide | 0.19 | 3.0 |
| Ex. 12 | | Tartaric acid-sodium hydroxide | 0.28 | 3.0 |
| Comp. Ex. 1 | 4.0 | Acetic acid-sodium acetate | 0.75 | 4.0 |

The results in Table 5 clearly show that, in the cases where the pH is in the predetermined range, regardless of the difference in the type of the buffer solution, the rate of generated rocuronium-related substance C after thermal treatment is markedly reduced, and the pH change is also markedly reduced.

Vascular Irritation Evaluation

The rocuronium preparation obtained in Example 6 (pH 2.5) and a commercial rocuronium preparation (trade name: ESLAX (registered trademark) Intravenous 50 mg/5.0 mL, acetate buffer solution, 0.15 M in terms of acetate ions, pH 4.0) (Comparative Example 2) were separately evaluated for the vascular irritation.

The results are shown in Table 6.

TABLE 6

| Preparation | ID No. | Finding | Time after administration (day) | | | | | | | | |
| --- | --- | --- | --- | --- | --- | --- | --- | --- | --- | --- | --- |
|  |  |  | 0 | 1 | 2 | 3 | 4 | 5 | 6 | 7 | 8 |
| Ex. 6 | 1 | Thrombus | − | − | − | − | − | − | − | − | − |
|  |  | Inflammation | − | − | − | − | − | − | − | − | − |
|  | 2 | Thrombus | − | − | − | − | − | − | − | − | − |
|  |  | Inflammation | − | − | − | − | − | − | − | − | − |
|  | 3 | Thrombus | − | − | − | − | − | − | − | − | − |
|  |  | Inflammation | − | − | − | − | − | − | − | − | − |
| Comp. Ex. 2 | 4 | Thrombus | − | − | − | − | − | − | − | − | − |
|  |  | Inflammation | − | − | − | − | − | − | − | − | − |
|  | 5 | Thrombus | − | − | − | − | − | − | − | − | + |
|  |  | Inflammation | − | + | − | − | − | − | − | − | − |
|  | 6 | Thrombus | − | − | − | − | − | − | − | − | − |
|  |  | Inflammation | − | − | − | − | − | − | − | − | − |

The results in Table 6 clearly show that, despite the pH lower than that of Comparative Example 2 as a commercial product, vascular irritation was not observed. Accordingly, in the present invention, the stability of a rocuronium preparation is increased without causing irritation of blood vessels.

Injection Pain Evaluation

The rocuronium preparation obtained, in Example 2 (pH 3.0), the rocuronium preparation obtained in Example 6 (pH 2.5), and Comparative Example 2 were separately evaluated for the injection pain.

The results are shown in Table 7 and FIG. 1.

TABLE 7

| Preparation | Integrated EMG (percentage relative to the value before administration) | |
| --- | --- | --- |
| | % | Standard error |
| Ex. 2 | 104.8 | 3.8 |
| Ex. 6 | 167.9 | 29.5 |
| Comp. Ex. 2 | 309.0 | 51.2 |

The results in Table 7 clearly show that, the rocuronium preparations of Examples 2 and 6, as compared to the commercial product, markedly reduced the injection pain to the degree of statistically significant difference. As a result, it was revealed that the present invention provides a rocuronium preparation which has an increased stability and does not cause injection pain.

INDUSTRIAL APPLICABILITY

The present invention, increases the stability (storage stability etc.) of a rocuronium preparation useful as a muscle relaxant or the like.

The invention claimed is:

1. A rocuronium preparation in a liquid form consisting of rocuronium and a buffer solution, and optionally a solvent and optionally an isotonizing agent, and having a pH of 1.8 to 3.5, wherein the buffer solution is at least one selected from the group consisting of a formate buffer solution, a citrate buffer solution, a tartrate buffer solution, a phthalate buffer solution, a phosphate buffer solution, a citric acid-phosphate buffer solution and a glycine buffer solution, and wherein the preparation is stable after 6 months of storage at 40° C. by generating 3% or less of a rocuronium-related substance C.

2. The rocuronium preparation of claim 1, having a pH of 2.5 to 3.5.

3. The rocuronium preparation of claim 1, having a pH of 2.8 to 3.2.

4. The rocuronium preparation of claim 1, wherein the buffer solution is at least one selected from the group consisting of a citric acid-sodium hydroxide buffer solution, a tartaric acid-sodium hydroxide buffer solution, a potassium hydrogen phthalate-hydrochloric acid buffer solution, and a glycine-hydrochloric acid buffer solution.

5. The rocuronium preparation of claim 1, wherein the pH is 2.5 to 3.5 and the buffer solution is a glycine-hydrochloric acid buffer solution of which the concentration is 0.01 M or higher.

6. A liquid rocuronium injection preparation consisting of rocuronium and a buffer solution, and optionally a solvent and optionally an isotonizing agent, and having a pH of 1.8 to 3.5, wherein the buffer solution is at least one selected from the group consisting of a formate buffer solution, a citrate buffer solution, a tartrate buffer solution, a phthalate buffer solution, a phosphate buffer solution, a citric acid-phosphate buffer solution and a glycine buffer solution, and wherein a rate of generated rocuronium-related substance C after 6-months storage at 40° C. is 3% or less.

7. The rocuronium preparation of claim 1, which is storable at room temperature.

8. A method for increasing or improving the stability of a rocuronium preparation, comprising adjusting the pH of a rocuronium preparation in a liquid form consisting of rocuronium and a buffer solution, and optionally a solvent and optionally an isotonizing agent, to 1.8 to 3.5, wherein the buffer solution is at least one selected from the group consisting of a formate buffer solution, a citrate buffer solution, a tartrate buffer solution, a phthalate buffer solution, a phosphate buffer solution, a citric acid-phosphate buffer solution and a glycine buffer solution, so that the rate of generated rocuronium-related substance C after 6-months storage at 40° C. is 3% or less.

9. A method for preventing or reducing both injection pain and vascular irritation caused by a rocuronium injection preparation and for increasing or improving the stability of the rocuronium injection preparation so that the rate of generated rocuronium-related substance C after 6-months storage at 40° C. is 3% or less, comprising adjusting the pH of a rocuronium injection preparation in a liquid form consisting of rocuronium and a buffer solution, and optionally a solvent and optionally an isotonizing agent, to 1.8 to 3.5, wherein the buffer solution is at least one selected from the group consisting of a formate buffer solution, a citrate buffer solution, a tartrate buffer solution, a phthalate buffer solution, a phosphate buffer solution, a citric acid-phosphate buffer solution and a glycine buffer solution, so that the rate of generated rocuronium-related substance C after 6-months storage at 40° C. is 3% or less.

10. The method of claim 8, wherein the preparation is prepared so as to be storable at room temperature.

* * * * *